United States Patent [19]

Maubru

[11] Patent Number: 6,090,162
[45] Date of Patent: Jul. 18, 2000

[54] COMPOSITION FOR THE OXIDATION DYEING OF KERATINOUS FIBRES COMPRISING A 5-SUBSTITUTED 3,4-DIAMINOPYRAZOLE AND A HALOGENATED META-AMINOPHENOL

[75] Inventor: Mireille Maubru, Chatou, France

[73] Assignee: L'Oreal S.A., Paris, France

[21] Appl. No.: 09/186,882

[22] Filed: Nov. 6, 1998

[30] Foreign Application Priority Data

Nov. 7, 1997 [FR] France .................................. 97 14051

[51] Int. Cl.$^7$ ...................................................... A61K 7/13
[52] U.S. Cl. ........................................ 8/409; 8/421; 8/423
[58] Field of Search ................................. 8/409, 421, 423

[56] References Cited

U.S. PATENT DOCUMENTS

| | | | |
|---|---|---|---|
| 4,976,742 | 12/1990 | Rose et al. | 8/421 |
| 5,061,289 | 10/1991 | Clausen et al. | 8/405 |
| 5,391,206 | 2/1995 | Cotteret | 8/408 |
| 5,430,159 | 7/1995 | Neunhoeffer et al. | 548/374.1 |
| 5,718,731 | 2/1998 | Loewe et al. | 8/409 |
| 5,766,576 | 6/1998 | Lowe et al. | 424/62 |
| 5,769,902 | 6/1998 | Samain | 8/409 |
| 5,785,717 | 7/1998 | Maubru et al. | 8/409 |

FOREIGN PATENT DOCUMENTS

| | | |
|---|---|---|
| 9 740 931 | 11/1996 | European Pat. Off. . |
| 2 586 913 | 3/1987 | France . |
| 2 748 274 | 11/1997 | France . |
| 3 843 892 | 6/1990 | Germany . |
| 4 234 885 | 4/1994 | Germany . |
| 4 234 886 | 4/1994 | Germany . |
| 4 234 887 | 4/1994 | Germany . |
| 4 422 603 | 1/1996 | Germany . |
| 195 43 988 | 5/1997 | Germany . |
| WO 96/15766 | 5/1996 | WIPO . |

OTHER PUBLICATIONS

English language translation of EP 39,030, Henkel, pp. 1–13, Nov. 1981.
English Language Derwent Abstract of DE 3 843 892, Jun. 1990.
English Language Derwent Abstract of DE 4 234 885, Apr. 1994.
English Language Derwent Abstract of DE 4 234 886, Apr. 1994.
English Language Derwent Abstract of DE 4 234 887, Apr. 1994.
English Language Derwent Abstract of DE 195 43 988, May 1997.
English Language Derwent Abstract of EP 0 740 931, Nov. 1996.
English Language Derwent Abstract of FR 2 586 913, Mar. 1987.
English Language Derwent Abstract of FR 2 748 274, Nov. 1997.

*Primary Examiner*—Caroline D. Liott
*Attorney, Agent, or Firm*—Finnegan, Henderson, Farabow, Garrett & Dunner, L.L.P.

[57] ABSTRACT

A composition for the oxidation dyeing of keratinous fibers, in particular of human keratinous fibers such as hair, with at least one 5-substituted 3,4-diaminopyrazole as an oxidation base, in combination with at least one meta-aminophenol halogenated at the ortho position of the phenol as a coupler, as well as a method of dyeing using this composition with an oxidizing agent.

23 Claims, No Drawings

COMPOSITION FOR THE OXIDATION DYEING OF KERATINOUS FIBRES COMPRISING A 5-SUBSTITUTED 3,4-DIAMINOPYRAZOLE AND A HALOGENATED META-AMINOPHENOL

The subject of the present invention is a composition for the oxidation dyeing of keratinous fibres, in particular of human keratinous fibres such as hair, which composition comprises at least one 5-substituted 3,4-diaminopyrazole as an oxidation base, in combination with at least one meta-aminophenol halogenated at the ortho position of the phenol as a coupler, as well as a method for dyeing keratinous fibres using this composition with an oxidizing agent.

It is known to dye keratinous fibres, and in particular human hair, with dyeing compositions containing oxidation dye precursors, in particular ortho- or para-phenylenediamines and ortho- or para-aminophenols or alternatively heterocyclic compounds such as pyrazole derivatives, which are generally called oxidation bases. The oxidation dye precursors, or oxidation bases, are colorless or weakly colored compounds which, when combined with oxidizing products, can give rise, by a process of oxidative condensation, to colored and coloring compounds.

It is also known that it is possible to vary the shades obtained with oxidation bases by combining them with suitably chosen couplers or color modifiers, where the latter may be chosen in particular from aromatic meta-diamines, meta-aminophenols, meta-diphenols and certain heterocyclic compounds.

The variety of molecules that can be used as oxidation bases and couplers allows a rich palette of colors to be obtained.

The so-called "permanent" color obtained by virtue of these oxidation dyes should, moreover, meet a number of requirements. It should have no toxicological drawbacks, and the dyes should obtain shades of the desired intensity and should exhibit good behaviour in relation to external agents, such as light, adverse weather conditions, washing, permanent waving, perspiration, and rubbing.

The dyes should also cover white hair and, finally, be the least selective possible, that is, to obtain the smallest possible color differences all along the same keratinous fibre, which may, indeed, be variously sensitized, i.e., damaged, between its end and its root.

There have already been proposed, in particular in German Patent Applications DE 3,843,892, DE 4,234,887, DE 4,234,886, DE 4,234,885 or DE 195 43 988, compositions for the oxidation dyeing of keratinous fibres containing, as an oxidation base, pyrazole derivatives such as 4,5-diaminopyrazoles, 3,4-diaminopyrazoles or 3,4,5-triaminopyrazoles, in combination with couplers conventionally used for oxidation dyeing, such as, for example, meta-phenylenediamines, meta-aminophenols, meta-diphenols and heterocyclic couplers such as, for example, indole derivatives. Such compositions are, however, not completely satisfactory especially from the point of view of the intensity of the colors obtained.

The inventors have now discovered that it is possible to obtain new intense dyes which are particularly resistant to the various attacks to which the hair may be subjected, by combining, as an oxidation base, at least one 5-substituted 3,4-diaminopyrazole of formula (I) defined below and, as a coupler, a meta-aminophenol halogenated at the ortho position of the phenol. This discovery forms the basis of the present invention.

The first subject of the invention is therefore a composition for the oxidation dyeing of keratinous fibres, and in particular of human keratinous fibres such as hair, characterized in that it comprises, in an appropriate medium for dyeing:

at least one oxidation base chosen from 5-substituted 3,4-diarninopyrazoles of the formula (I), and their acid addition salts:

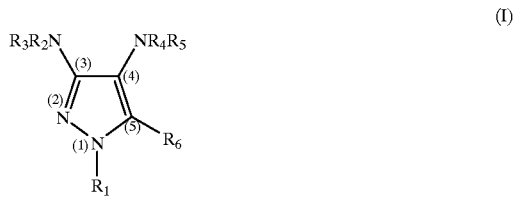

(I)

in which:
$R_1$, $R_2$, $R_3$, $R_4$ and $R_5$, which are identical or different, represent a hydrogen atom; a linear or branched $C_1$–$C_6$ alkyl radical; a $C_2$–$C_4$ hydroxyalkyl radical; a $C_2$–$C_4$ aminoalkyl radical; a phenyl radical; a phenyl radical substituted with a halogen atom or a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy, hydroxyl, $C_1$–$C_4$ hydroxyalkyl, amino or $C_1$–$C_4$ alkylamino radical; at most one of the $R_2$ to $R_5$ radicals may designate a radical

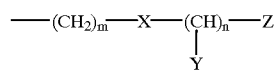

in which m and n are integers, which are identical or different, and range from 1 to 3 inclusive, X represents an oxygen atom or alternatively the group NH, Y represents a hydrogen atom or alternatively a methyl radical, and Z represents a methyl radical, an OR or NRR' group in which R and R', which may be identical or different, designate a hydrogen atom, a methyl radical or an ethyl radical;

it being understood that when $R_2$ represents a hydrogen atom, then $R_3$ may also represent an amino or $C_1$–$C_4$ alkylamino radical;

$R_6$ represents a linear or branched $C_1$–$C_6$ alkyl radical; a $C_1$–$C_6$ alkoxy radical; a $C_1$–$C_4$ hydroxyalkyl radical; a $C_1$–$C_4$ hydroxyalkylamino radical; a $C_1$–$C_4$ aminoalkyl radical; a phenyl radical; a phenyl radical substituted with a halogen atom or with a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, nitro, trifluoromethyl, amino or $C_1$–$C_4$ alkylamino radical; a heterocycle chosen from thiophene, furan and pyridine, or alternatively a radical —$(CH_2)_p$—O—$(CH_2)_q$—OR", in which p and q are integers, which are identical or different, and range from 1 to 3 inclusive and R" represents a hydrogen atom or a methyl radical, it being understood that in the formula (I) above:

at least one of the $R_4$ and $R_5$ radicals represents a hydrogen atom, when $R_2$, and/or $R_4$, represents a substituted or unsubstituted phenyl radical, or a benzyl radical or a radical

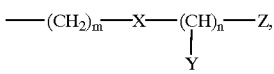

then $R_3$, and/or $R_5$, cannot represent any of these three foregoing radicals, $R_1$ may also represent a heterocyclic residue 2-, 3- or 4-pyridyl, 2- or 3-thienyl, 2- or 3-furyl optionally substituted with a methyl radical, and at least one coupler chosen from the halogenated meta-aminophenols of the formula (II), and their acid addition salts:

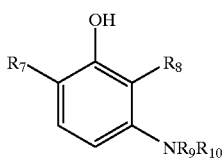
(II)

in which:

$R_7$ and $R_8$, which may be identical or different, represent a hydrogen atom, a halogen atom such as chlorine, bromine, iodine or fluorine, a $C_1$–$C_4$ alkyl, $C_1$–$C_4$ monohydroxyalkyl, $C_2$–$C_4$ polyhydroxyalkyl, $C_1$–$C_4$ alkoxy, $C_1$–$C_4$ monohydroxyalkoxy or $C_2$–$C_4$ polyhydroxyalkoxy radical;

$R_9$ and $R_{10}$, which may be identical or different, represent a hydrogen atom, a $C_1$–$C_4$ alkyl, $C_1$–$C_4$ monohydroxyalkyl, $C_2$–$C_4$ polyhydroxyalkyl or $C_1$–$C_4$ monoaminoalkyl radical;

where at least one of the $R_7$ and $R_8$ radicals represents a halogen atom.

Further aspects of the invention include methods of dyeing keratinous fibers, various forms of the compositions of the invention, and multicompartment devices and kits for the compositions.

Additional features and advantages of the invention are set forth in the description that follows, and in part will be apparent from the description or may be learned from the practice of the invention. Both the foregoing general description and the following detailed description of the invention are exemplary and explanatory only and are not restrictive of the claimed invention.

The oxidation dye composition of the present invention obtains intense colors with a variety of shades, which are not very selective and which exhibit excellent properties of resistance both to atmospheric agents such as light and adverse weather conditions and to perspiration and various treatments to which the hair may be subjected (shampoos, permanent wavings).

Among the $C_1$–$C_4$ alkyl and $C_1$–$C_4$ alkoxy radicals of the compounds of formulae (I) and (II) above, the methyl, ethyl, propyl, methoxy and ethoxy radicals are preferred.

The 5-substituted 3,4-diaminopyrazoles are compounds known in the prior art, which can be prepared, for example according to the methods of preparation described in French Patent Application FR-A-2,748,274, the disclosure of which is hereby incorporated by reference.

Among the 5-substituted 3,4-diaminopyrazoles of formula (I) which can be used as oxidation bases in the dyeing compositions in accordance with the invention, preferred compounds include:

3,4-diamino-5-ethylpyrazole;
3,4-diamino-5-methylpyrazole;
3,4-diamino-5-isopropylpyrazole;
3,4-diamino-5-tert-butylpyrazole;
3,4-diamino-5-phenylpyrazole;
3,4-diamino-5-methoxypyrazole;
3,4-diamino-5-(4'-methoxyphenyl)pyrazole;
3,4-diamino-5-(3'-methoxyphenyl)pyrazole;
3,4-diamino-5-(2'-methoxyphenyl)pyrazole;
3,4-diamino-5-(4'-methylphenyl)pyrazole;
3,4-diamino-5-(3'-methylphenyl)pyrazole;
3,4-diamino-5-(2'-chlorophenyl)pyrazole;
3,4-diamino-5-(4'-chlorophenyl)pyrazole;
3,4-diamino-5-(3'-trifluoromethylphenyl)pyrazole;
3,4-diamino-1,5-dimethylpyrazole;
3,4-diamino-5-ethyl-1-methylpyrazole;
3,4-diamino-1-methyl-5-tert-butylpyrazole;
3,4-diamino-1-methyl-5-phenylpyrazole;
3,4-diamino-1-methyl-5-methoxypyrazole;
3,4-diamino-1-methyl-5-(4'-methoxyphenyl)pyrazole;
3,4-diamino-1-methyl-5-(3'-methoxyphenyl)pyrazole;
3,4-diamino-1-methyl-5-(2'-methoxyphenyl)pyrazole;
3,4-diamino-1-methyl-5-(4'-methylphenyl)pyrazole;
3,4-diamino-1-methyl-5-(3'-methylphenyl)pyrazole;
3,4-diamino-5-(2'-chlorophenyl)-1-methylpyrazole;
3,4-diamino-5-(4'-chlorophenyl)-1-methyl pyrazole;
3,4-diamino-5-(3'-trifluoromethylphenyl)-1-methylpyrazole;
3,4-diamino-1-ethyl-5-methylpyrazole;
3,4-diamino-1,5-diethylpyrazole;
3,4-diamino-1-ethyl-5-tert-butylpyrazole;
3,4-diamino-1-ethyl-5-phenylpyrazole;
3,4-diamino-1-ethyl-5-methoxypyrazole;
3,4-diamino-1-ethyl-5-(4'-methoxyphenyl)pyrazole;
3,4-diamino-1-ethyl-5-(3'-methoxyphenyl)pyrazole;
3,4-diamino-1-ethyl-5-(2'-methoxyphenyl)pyrazole;
3,4-diamino-1-ethyl-5-(4'-methylphenyl)pyrazole;
3,4-diamino-1-ethyl-5-(3'-methylphenyl)pyrazole;
3,4-diamino-5-(2'-chlorophenyl)-1-ethylpyrazole;
3,4-diamino-5-(4'-chlorophenyl)-1-ethylpyrazole;
3,4-diamino-1-ethyl-5-(3'-trifluoromethylphenyl)pyrazole;
3,4-diamino-1-isopropyl-5-methylpyrazole;
3,4-diamino-5-ethyl-1-isopropylpyrazole;
3,4-diamino-1-isopropyl-5-tert-butylpyrazole;
3,4-diamino-1-isopropyl-5-phenylpyrazole;
3,4-diamino-1-isopropyl-5-methoxypyrazole;
3,4-diamino-1-isopropyl-5-(4'-methoxyphenyl)pyrazole;
3,4-diamino-1-isopropyl-5-(3'-methoxyphenyl)pyrazole;
3,4-diamino-1-isopropyl-5-(2'-methoxyphenyl)pyrazole;
3,4-diamino-1-isopropyl-5-(4'-methylphenyl)pyrazole;
3,4-diamino-1-isopropyl-5-(3'-methylphenyl)pyrazole;
3,4-diamino-5-(2'-chlorophenyl)-1-isopropylpyrazole;
3,4-diamino-5-(4'-chlorophenyl)-1-isopropylpyrazole;
3,4-diamino-1-isopropyl-5-(3'-trifluoromethylphenyl)pyrazole;
3,4-diamino-5-methyl-1-propylpyrazole;
3,4-diamino-5-ethyl-1-propylpyrazole;
3,4-diamino-1-propyl-5-tert-butylpyrazole;
3,4-diamino-5-phenyl-1-propylpyrazole;
3,4-diamino-5-methoxy-1-propylpyrazole;
3,4-diamino-5-(4'-methoxyphenyl)-1-propylpyrazole;
3,4-diamino-5-(3'-methoxyphenyl)-1-propylpyrazole;
3,4-diamino-5-(2'-methoxyphenyl)-1-propylpyrazole;
3,4-diamino-5-(4'-methylphenyl)-1-propylpyrazole;
3,4-diamino-5-(3'-methylphenyl)-1-propylpyrazole;
3,4-diamino-5-(2'-chlorophenyl)-1-propylpyrazole;
3,4-diamino-5-(4'-chlorophenyl)-1-propylpyrazole;

3,4-diamino-1-propyl-5-(3'-trifluoromethylphenyl)pyrazole;
1-benzyl-3,4-diamino-5-methylpyrazole;
1-benzyl-3,4-diamino-5-ethylpyrazole;
1-benzyl-3,4-diamino-5-tert-butylpyrazole;
1-benzyl-3,4-diamino-5-phenylpyrazole;
1-benzyl-3,4-diamino-5-methoxypyrazoie;
1-benzyl-3,4-diamino-5-(4'-methoxyphenyl)pyrazole;
1-benzyl-3,4-diamino-5-(3'-methoxyphenyl)pyrazole;
1-benzyl-3,4-diamino-5-(2'-methoxyphenyl)pyrazole;
1-benzyl-3,4-diamino-5-(4'-methylphenyl)pyrazole;
1-benzyl-3,4-diamino-5-(3'-methylphenyl)pyrazole;
1-benzyl-3,4-diamino-5-(2'-chlorophenyl)pyrazole;
1-benzyl-3,4-diamino-5-(4'-chlorophenyl)pyrazole;
1-benzyl-3,4-diamino-5-(3'-trifluoromethylphenyl) pyrazole;
1-[4'-chlorobenzyl]-3,4-diamino-5-methylpyrazole;
1-[4'-chlorobenzyl]-3,4-diamino-5-ethylpyrazole;
1-[4'-chlorobenzyl]-3,4-diamino-5-tert-butylpyrazole;
1-[4'-chlorobenzyl]-3,4-diamino-5-phenylpyrazole;
1-[4'-chlorobenzyl]-3,4-diamino-5-methoxypyrazole;
1-[4'-chlorobenzyl]-3,4-diamino-5-(4'-methoxyphenyl) pyrazole;
1-[4'-chlorobenzyl]-3,4-diamino-5-(3'-methoxyphenyl) pyrazole;
1-[4'-chlorobenzyl]-3,4-diamino-5-(2'-methoxyphenyl) pyrazole;
1-[4'-chlorobenzyl]-3,4-diamino-5-(4'-methylphenyl) pyrazole;
1-[4'-chlorobenzyl]-3,4-diamino-5-(3'-methylphenyl) pyrazole;
1-[4'-chlorobenzyl]-3,4-diamino-5-(2'-chlorophenyl) pyrazole;
1-[4'-chlorobenzyl]-3,4-diamino-5-(4'-chlorophenyl) pyrazole;
1-[4'-chlorobenzyl]-3,4-diamino-5-(3'-trifluoromethylphenyl)pyrazole;
3,4-diamino-5-hydroxymethyl-1-methylpyrazole;
3,4-diamino-5-hydroxymethyl-1-ethyl pyrazole;
3,4-diamino-5-hydroxymethyl-1-isopropylpyrazole;
3,4-diamino-5-hydroxymethyl-1-propylpyrazole;
1-benzyl-3,4-diamino-5-hydroxymethylpyrazole;
1-[4'-chlorobenzyl]-3,4-diamino-5-hydroxymethylpyrazole;
5-aminomethyl-3,4-diamino-1-methylpyrazole;
5-aminomethyl-3,4-diamino-1-ethylpyrazole;
5-aminomethyl-3,4-diamino-1-isopropylpyrazole;
5-aminomethyl-3,4-diamino-1-propylpyrazole;
5-aminomethyl-1-benzyl-3,4-diaminopyrazole;
5-aminomethyl-1-[4'-chlorobenzyl]-3,4-diaminopyrazole;
3,4-diamino-5-hydroxymethylpyrazole;
3,4-diamino-5-[β-hydroxyethylamino]-1-methylpyrazole;
3,4-diamino-5-[β-hydroxyethylamino]-1-ethylpyrazole;
3,4-diamino-5-[β-hydroxyethylamino]-1-isopropylpyrazole;
3,4-diamino-5-[β-hydroxyethylamino]-1-propylpyrazole;
3,4-diamino-5-[β-hydroxyethylamino]pyrazole;
1-benzyl-3,4-diamino-5-[β-hydroxyethylamino]pyrazole;
1-[4'-chlorobenzyl]-3,4-diamino-5-[β-hydroxyethylamino] pyrazole;
3,4-diamino-5-isopropyl-1-methylpyrazole;
and their acid addition salts.

Among these 5-substituted 3,4-diaminopyrazoles, more particularly preferred are:
3,4-diamino-5-methylpyrazole;
3,4-diamino-5-ethylpyrazole;
3,4-diamino-5-isopropylpyrazole;
3,4-diamino-5-tert-butylpyrazole;
3,4-diamino-5-phenylpyrazole;
3,4-diamino-5-(4'-methoxyphenyl)pyrazole;
3,4-diamino-5-(3'-methoxyphenyl)pyrazole;
3,4-diamino-5-(2'-methoxyphenyl)pyrazole;
3,4-diamino-5-(4'-methyl phenyl)pyrazole;
3,4-diamino-5-(3'-methylphenyl)pyrazole;
5-(2'-chlorophenyl)-3,4-diaminopyrazole;
5-(4'-chlorophenyl)-3,4-diaminopyrazole;
3,4-diamino-1,5-dimethylpyrazole;
3,4-diamino-5-ethyl-1-methylpyrazole;
3,4-diamino-5-isopropyl-1-methylpyrazole;
3,4-diamino-1-methyl-5-tert-butylpyrazole;
3,4-diamino-1-methyl-5-phenylpyrazole;
3,4-diamino-1-methyl-5-methoxypyrazole;
3,4-diamino-1-methyl-5-(4'-methoxyphenyl)pyrazole;
3,4-diamino-1-methyl-5-(3'-methoxyphenyl)pyrazole;
3,4-diamino-1-methyl-5-(2'-methoxyphenyl)pyrazole;
3,4-diamino-1 -methyl-5-(4'-methylphenyl)pyrazole;
3,4-diamino-1-methyl-5-(3'-methylphenyl)pyrazole;
5-(2'-chlorophenyl)-3,4-diamino-1-methylpyrazole;
5-(4'-chlorophenyl)-3,4-diamino-1-methylpyrazole;
and their acid addition salts.

Among the halogenated meta-aminophenols of formula (II) which can be used as couplers in the dyeing compositions of the present invention, preferred compounds include 3-amino-6-chlorophenol, 3-amino-6-bromophenol, 3-(β-aminoethyl)amino-6-chlorophenol, 3-(β-hydroxyethyl)amino-6-chlorophenol, 3-amino-2-chloro-6-methylphenol, and their acid addition salts.

The 5-substituted 3,4-diaminopyrazole(s) of formula (I) and/or the corresponding acid addition salt(s) preferably represent approximately from 0.0005 to 12% by weight of the total weight of the dyeing composition, and still more preferably approximately from 0.005 to 6% by weight of this total weight.

The halogenated meta-aminophenol(s) of formula (II) of the present invention and/or the corresponding acid addition salt(s) preferably represent approximately from 0.0001 to 5% by weight of the total weight of the dyeing composition, and still more preferably approximately from 0.005 to 3% by weight of this total weight.

In general, the acid addition salts which can be used in accordance with dyeing compositions of the invention, as oxidation bases and couplers, are chosen in particular from hydrochlorides, hydrobromides, sulphates and tartrates, lactates and acetates.

The dyeing compositions of the present invention may contain other oxidated bases conventionally used for oxidation dyeing, various 5-substituted 3,4-diaminopyrazoles of formula (I) and/or other couplers conventionally used for oxidation dyeing, various halogenated meta-aminophenols of formula (II), and/or direct dyes, in particular to modify the shades or to enrich the shimmer of the color obtained.

The appropriate medium for dyeing (or carrier) generally contains water or a mixture of water and at least one organic solvent for solubilizing the components that are not sufficiently soluble in water. Examples of organic solvent include, for example, the $C_1$–$C_4$ lower alkanols such as ethanol and isopropanol; glycerol; glycols or glycol ethers such as 2-butoxyethanol, propylene glycol, propylene glycol monomethyl ether, diethylene glycol monoethyl ether and monomethyl ether, as well as aromatic alcohols such as benzyl alcohol and phenoxyethanol, analogous products and mixtures thereof.

The solvent(s) may be present in proportions preferably ranging from about 1 to about 40% by weight relative to the total weight of the dyeing composition, and still more preferably from about 5 to about 30% by weight.

The pH of the dyeing composition of the present invention generally ranges from approximately 3 to approximately 12 and still more preferably from approximately 5 to approximately 11. The pH may be adjusted to the desired value by means of acidifying or alkalinizing agents normally used in dyeing keratinous fibres.

Examples of acidifying agents include for example, inorganic or organic acids such as hydrochloric acid, orthophosphoric acid, carboxylic acids such as tartaric acid, citric acid, lactic acid and sulphonic acids.

Examples of alkalinizing agents include ammonium hydroxide, alkali metal carbonates, alkanolamines such as mono-, di- and triethanolamines as well as derivatives thereof, sodium or potassium hydroxides and the compounds of the formula (III):

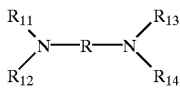

(III)

in which R is a propylene residue optionally substituted with a hydroxyl group or a $C_1$–$C_4$ alkyl radical; $R_{11}$, $R_{12}$, $R_{13}$ and $R_{14}$, which are identical or different, represent a hydrogen atom or a $C_1$–$C_4$ alkyl or $C_1$–$C_4$ hydroxyalkyl radical.

The dyeing compositions of the present invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickening agents, antioxidants, penetrating agents, sequestering agents, perfumes, buffers, dispersing agents, conditioning agents such as for example silicones modified or unmodified, volatile or nonvolatile silicones, film-forming agents, ceramides, preservatives and opacifying agents.

Of course, persons skilled in the art will take care to choose this or these possible additional compounds, such that the advantageous properties intrinsically attached to the combination in accordance with the invention are not, or are not substantially, altered by the addition(s) envisaged.

The dyeing compositions of the present invention may be provided in various forms, such as in the form of liquids, creams, gels or any other form appropriate for dyeing keratinous fibres, and especially human hair.

Another subject of the invention is a method of dyeing keratinous fibres, and in particular human keratinous fibres such as hair, using the dyeing composition defined above.

According to a preferred method, the dyeing composition defined above is applied to the fibres, the color being developed at acidic, neutral or alkaline pH with the aid of an oxidizing agent which is added right at the time of use to the dyeing composition or which is present in an oxidizing composition applied simultaneously with or sequentially to the dyeing composition.

According to a particularly preferred embodiment of the dyeing method according to the invention, the dyeing composition described above is mixed, at the time of use, with an oxidizing composition containing, in an appropriate medium for dyeing, at least one oxidizing agent present in a sufficient quantity to develop a color. The mixture obtained is then applied to the keratinous fibres and left for approximately 3 to approximately 60 minutes, preferably for approximately 5 to approximately 40 minutes, after which they are rinsed, washed with a shampoo, rinsed again and dried.

The oxidizing agent present in the oxidizing composition as defined above may be chosen from oxidizing agents conventionally used for the oxidation dyeing of keratinous fibres, and preferably including hydrogen peroxide, urea peroxide, alkali metal bromates, persalts such as perborates, percarbonates and persulphates, and peracids. Hydrogen peroxide is particularly preferred.

The pH of the oxidizing composition containing the oxidizing agent as defined above is chosen such that after mixing with the dyeing composition, the pH of the resulting composition applied to the keratinous fibres preferably varies from approximately 3 to approximately 12 and still more preferably from approximately 5 to approximately 11. The pH can be adjusted to the desired value by means of acidifying or alkalinizing agents normally used in dyeing keratinous fibres and as defined above.

The oxidizing composition as defined above may also contain various adjuvants conventionally used in compositions for dyeing hair and as defined above.

The composition which is finally applied to the keratinous fibres may be provided in various forms, such as in the form of liquids, creams, gels, or in any other form appropriate for dyeing keratinous fibres, and in particular human hair.

Another subject of the invention is a multicompartment device or multicompartment dyeing "kit" or any other multicompartment packaging system in which a first compartment contains the dyeing composition defined above and a second compartment contains the oxidizing composition defined above. These devices may be equipped with means which allow the desired mixture to be delivered to the hair, such as the devices described in patent FR 2,586,913 in the name of L'Oreal, which disclosure is incorporated herein by reference.

The present invention is further illustrated by the following examples which are designed to teach those of ordinary skill in the art how to practice the invention. The following examples are merely illustrative of the invention and should not be construed as limiting the invention as claimed.

EXAMPLES

COMPARATIVE EXAMPLES OF DYES

The following dyeing compositions of the present invention were prepared (amounts in grams):

|  | EXAMPLE | | | |
| --- | --- | --- | --- | --- |
|  | 1 (*) | 2 | 3 | 4 |
| 3,4-Diamino-5-methyl-pyrazole dihydrochloride (oxidation base) | 0.555 | 0.555 | 0.555 | 0.555 |
| 3-Aminophenol (coupler not forming part of the invention) | 0.327 | — | — | — |
| 3-Amino-6-chlorophenol (coupler in accordance with the invention) | — | 0.431 | — | — |
| 3-(β-Aminoethyl)amino-6-chlorophenol (coupler in accordance with the invention) | — | — | 0.560 | — |
| 3-Amino-2-chloro-6-methylphenol | — | — | — | 0.473 |

-continued

| | EXAMPLE | | | |
|---|---|---|---|---|
| | 1 (*) | 2 | 3 | 4 |
| (coupler in accordance with the invention) | | | | |
| Common dye carrier | () | () | () | () |
| Demineralized water qs | 100 g | 100 g | 100 g | 100 g |

(*): Example not forming part of the invention
(**): Common dye carrier:
Polyglycerolated oleyl alcohol containing 2 moles of glycerol 4.0 g
Polyglycerolated oleyl alcohol containing 4 moles of glycerol, containing 78% active materials (A.M.) 5.69 g A.M.
Oleic acid 3.0 g
Oleylamine containing 2 moles of ethylene oxide sold under the trade name ETHOMEEN 012 by the company AKCO 7.0 g
Diethylaminopropyl laurylaminosuccinamate, sodium salt, containing 55% of A.M. 30 g A.M.
Oleyl alcohol 5.0 g
Oleic acid diethanolamide 12.0 g
Propylene glycol 3.5 g
Ethyl alcohol 7.0 g
Dipropylene glycol 0.5 g
Proylene glycol monomethyl ether 9.0 g
Sodium metabisulphite in aqueous solution containing 35% A.M. 0.455 g A.M.
Ammonium acetate 0.8 g
Antioxidant, sequestrant qs
Perfume, preservative qs
Aqueous ammonia containing 20% $NH_3$ 10 g It is important to note that each of the dyeing compositions 1 to 4 above contain the same molar quantity of coupler, namely $3 \times 10^{-3}$ mole.

At the time of use, each dyeing composition above was mixed with an equal quantity by weight of an oxidizing composition containing a solution of hydrogen peroxide at 20 volumes (6% by weight).

Each resultant composition was applied for 30 minutes to a lock of permanently waved grey hair which was 90% white. The hair locks were then rinsed, washed with a standard shampoo and then dried.

The color of the locks was evaluated before and after dyeing, using the MUNSELL system, by means of a MINOLTA CM 2002 calorimeter so as to determine the intensity of the colors obtained with each of the compositions described above.

The difference between the color of the lock before dyeing and the color of the lock after dyeing was calculated by applying the NICKERSON formula:

$$\Delta E = 0.4 \, Co\Delta H + 6\Delta V + 3\Delta C$$

as described for example in "Couleur, Industrie et Technique"; pages 14–17; Vol. No. 5; 1978.

In this formula, $\Delta E$ represents the difference in color between two locks, $\Delta H$, $\Delta V$ and $\Delta C$ represent the variation in the absolute value of the parameters H, V and C, and Co represents the purity of the lock relative to which it is desired to evaluate the color difference. The higher the figure indicated, the more intense the color ($\Delta E$).

The results are given in Table I below:

TABLE I

| EXAMPLE | Hair color before dyeing | Hair color after dyeing | Color intensity | | | |
|---|---|---|---|---|---|---|
| | | | $\Delta H$ | $\Delta V$ | $\Delta C$ | $\Delta E$ |
| 1(*) | 4.0 Y 5.1/1.5 | 3.6 R 3.2/3.4 | 20.4 | 1.9 | 1.9 | 29.3 |
| 2 | 4.0 Y 5.1/1.5 | 6.4 RP 2.5/3.4 | 27.6 | 2.6 | 1.9 | 37.9 |
| 3 | 4.0 Y 5.1/1.5 | 6.8 RP 2.6/2.7 | 27.2 | 2.5 | 1.2 | 34.9 |
| 4 | 4.0 Y 5.1/1.5 | 0.1 R 2.6/4.5 | 23.9 | 2.5 | 3.0 | 38.3 |

(*): Example not forming part of the invention.

These results show that the color obtained using the dyeing composition of Example 1 not forming part of the invention as a result of containing the combination of a 5-substituted 3,4-diaminopyrazole and a nonhalogenated meta-aminophenol, led to a color which was considerably less intense than the colors obtained using the compositions of Examples 2 to 4, all forming part of the invention as, a result of containing the combination of a 5-substituted 3,4-diaminopyrazole and a meta-aminophenol halogenated at the ortho position of the phenol.

The foregoing written description relates to various embodiments of the present invention. Numerous changes and modifications may be made therein without departing from the spirit and scope of the invention as defined in the following claims.

What is claimed is:

1. A composition for the oxidation dyeing of keratinous fibres, in an appropriate medium for dyeing, said composition comprising:

an oxidation base, said oxidation base being a 5-substituted 3,4-diaminopyrazole of formula I or an acid addition salt thereof:

$$\text{(I)}$$

in which:
$R_1$, $R_2$, $R_3$, $R_4$ and $R_5$ are identical or different and represent a hydrogen atom; a linear or branched $C_1$–$C_6$ alkyl radical; a $C_2$–$C_4$ hydroxyalkyl radical; a $C_2$–$C_4$ aminoalkyl radical; a phenyl radical; a phenyl radical substituted with a halogen atom or a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy, hydroxyl, $C_1$–$C_4$ hydroxyalkyl, amino or $C_1$–$C_4$ alkylamino radical;
at most one of the radicals $R_2$ to $R_5$ represents a radical $$-(CH_2)_m-X-(CH_n)_n-Z$$
$$\phantom{-(CH_2)_m-X-(}|$$
$$\phantom{-(CH_2)_m-X-(CH}Y$$

in which m and n are integers that are identical or different and range from 1 to 3 inclusive,
X represents an oxygen atom or the group NH,
Y represents a hydrogen atom or a methyl radical, and Z represents a methyl radical, an OR or NRR' group in which R and R' are identical or different and represent a hydrogen atom, a methyl radical or an ethyl radical;

with the proviso that when $R_2$ represents a hydrogen atom, $R_3$ may also represent an amino or $C_1$–$C_4$ alkylamino radical;

$R_6$ represents a linear or branched $C_1$–$C_6$ alkyl radical; a $C_1$–$C_6$ alkoxyradical; a $C_1$–$C_4$ hydroxyalkyl radical; $C_1$–$C_4$ hydroxyalkylamino radical; a $C_1$–$C_4$ aminoalkyl radical; a phenyl radical; a phenyl radical substituted with a halogen atom or with a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, nitro, trifluoromethyl, amino or $C_1$–$C_4$ alkylamino radical; a heterocycle selected from thiophene, furan and pyridine; or a radical —$(CH_2)_p$—O—$(CH_2)_q$—OR", in which p and q are integers that are identical or different and range from 1 to 3 inclusive and R" represents a hydrogen atom or a methyl radical, with the proviso that in the formula I above:
at least one of the $R_4$ and $R_5$ radicals represents a hydrogen atom, and
when $R_2$ represents a substituted or unsubstituted phenyl radical, a benzyl radical or a radical

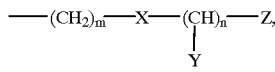

then $R_3$ does not represent any of these three radicals, and
when $R_4$ represents a substituted or unsubstituted phenyl radical, a benzyl radical or a radical

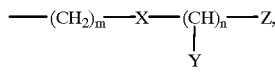

then $R_5$ does not represent any of these three radicals,
or $R_1$ represents a heterocyclic residue selected from 2-, 3- or 4-pyridyl, 2- or 3-thienyl, and 2- or 3-furyl unsubstituted or substituted with a methyl radical, and at least one coupler, said coupler being a halogenated meta-aminophenol of formula II, or an acid addition salt thereof:

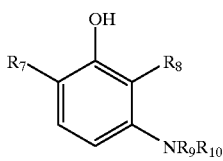

(II)

in which:
$R_7$ and $R_8$ are identical or different and represent a hydrogen atom, a halogen atom, a $C_1$–$C_4$ alkyl, $C_1$–$C_4$ monohydroxyalkyl, $C_2$–$C_4$ polyhydroxyalkyl, $C_1$–$C_4$ alkoxy, $C_1$–$C_4$ monohydroxyalkoxy or $C_2$–$C_4$ polyhydroxyalkoxy radical;

$R_9$ and $R_{10}$ are identical or different and represent a hydrogen atom, a $C_1$–$C_4$ alkyl, $C_1$–$C_4$ monohydroxyalkyl, $C_2$–$C_4$ polyhydroxyalkyl or $C_1$–$C_4$ monoaminoalkyl radical; and at least one of the $R_7$ and $R_8$ radicals represents a halogen atom.

2. A composition according to claim 1, wherein $R_7$ and $R_8$ are identical or different and represent chlorine, bromine, iodine or fluorine.

3. A composition according to claim 1, wherein the keratinous fibres are human keratinous fibres.

4. A composition according to claim 3, wherein the keratinous fibres are human hair.

5. A composition according to claim 1, wherein the 5-substituted 3,4-diaminopyrazole of formula I is:

3,4-diamino-5-ethylpyrazole;
3,4-diamino-5-methylpyrazole;
3,4-diamino-5-isopropylpyrazole;
3,4-diamino-5-tert-butylpyrazole;
3,4-diamino-5-phenylpyrazole;
3,4-diamino-5-methoxypyrazole;
3,4-diamino-5-(4'-methoxyphenyl)pyrazole;
3,4-diamino-5-(3'-methoxyphenyl)pyrazole;
3,4-diamino-5-(2'-methoxyphenyl)pyrazole;
3,4-diamino-5-(4'-methylphenyl)pyrazole;
3,4-diamino-5-(3'-methylphenyl)pyrazole;
3,4-diamino-5-(2'-chlorophenyl)pyrazole;
3,4-diamino-5-(4'-chlorophenyl)pyrazole;
3,4-diamino-5-(3'-trifluoromethylphenyl)pyrazole;
3,4-diamino-1,5-dimethylpyrazole;
3,4-diamino-5-ethyl-1-methylpyrazole;
3,4-diamino-1-methyl-5-tert-butylpyrazole;
3,4-diamino-1-methyl-5-phenylpyrazole;
3,4-diamino-1-methyl-5-methoxypyrazole;
3,4-diamino-1-methyl-5-(4'-methoxyphenyl)pyrazole;
3,4-diamino-1-methyl-5-(3'-methoxyphenyl)pyrazole;
3,4-diamino-1-methyl-5-(2'-methoxyphenyl)pyrazole;
3,4-diamino-1-methyl-5-(4'-methylphenyl)pyrazole;
3,4-diamino-1-methyl-5-(3'-methylphenyl)pyrazole;
3,4-diamino-5-(2'-chlorophenyl)-1-methylpyrazole;
3,4-diamino-5-(4'-chlorophenyl)-1-methylpyrazole;
3,4-diamino-5-(3'-trifluoromethylphenyl)-1-methylpyrazole;
3,4-diamino-1-ethyl-5-methylpyrazole;
3,4-diamino-1,5-diethylpyrazole;
3,4-diamino-1-ethyl-5-tert-butylpyrazole;
3,4-diamino-1-ethyl-5-phenylpyrazole;
3,4-diamino-1-ethyl-5-methoxypyrazole;
3,4-diamino-1-ethyl-5-(4'-methoxyphenyl)pyrazole;
3,4-diamino-1-ethyl-5-(3'-methoxyphenyl)pyrazole;
3,4-diamino-1-ethyl-5-(2'-methoxyphenyl)pyrazole;
3,4-diamino-1-ethyl-5-(4'-methylphenyl)pyrazole;
3,4-diamino-1-ethyl-5-(3'-methylphenyl)pyrazole;
3,4-diamino-5-(2'-chlorophenyl)-1-ethylpyrazole;
3,4-diamino-5-(4'-chlorophenyl)-1-ethylpyrazole;
3,4-diamino-1-ethyl-5-(3'-trifluoromethylphenyl)pyrazole;
3,4-diamino-1-isopropyl-5-methylpyrazole;
3,4-diamino-5-ethyl-1-isopropylpyrazole;
3,4-diamino-1-isopropyl-5-tert-butylpyrazole;
3,4-diamino-1-isopropyl-5-phenylpyrazole;
3,4-diamino-1-isopropyl-5-methoxypyrazole;

3,4-diamino-1-isopropyl-5-(4'-methoxyphenyl)pyrazole;
3,4-diamino-1-isopropyl-5-(3'-methoxyphenyl)pyrazole;
3,4-diamino-1-isopropyl-5-(2'-methoxyphenyl)pyrazole;
3,4-diamino-1-isopropyl-5-(4'-methylphenyl)pyrazole;
3,4-diamino-1-isopropyl-5-(3'-methylphenyl)pyrazole;
3,4-diamino-5-(2'-chlorophenyl)-1-isopropylpyrazole;
3,4-diamino-5-(4'-chlorophenyl)-1-isopropylpyrazole;
3,4-diamino-1-isopropyl-5-(3'-trifluoromethylphenyl) pyrazole;
3,4-diamino-5-methyl-1-propylpyrazole;
3,4-diamino-5-ethyl-1-propylpyrazole;
3,4-diamino-1-propyl-5-tert-butylpyrazole;
3,4-diamino-5-phenyl-1-propylpyrazole;
3,4-diamino-5-methoxy-1-propylpyrazole;
3,4-diamino-5-(4'-methoxyphenyl)-1-propylpyrazole;
3,4-diamino-5-(3'-methoxyphenyl)-1-propylpyrazole;
3,4-diamino-5-(2'-methoxyphenyl)-1-propylpyrazole;
3,4-diamino-5-(4'-methylphenyl)-1-propylpyrazole;
3,4-diamino-5-(3'-methylphenyl)-1-propylpyrazole;
3,4-diamino-5-(2'-chlorophenyl)-1-propylpyrazole;
3,4-diamino-5-(4'-chlorophenyl)-1-propylpyrazole;
3,4-diamino-1-propyl-5-(3'-trifluoromethylphenyl) pyrazole;
1-benzyl-3,4-diamino-5-methylpyrazole;
1-benzyl-3,4-diamino-5-ethylpyrazole;
1-benzyl-3,4-diamino-5-tert-butylpyrazole;
1-benzyl-3,4-diamino-5-phenylpyrazole;
1-benzyl-3,4-diamino-5-methoxypyrazole;
1-benzyl-3,4-diamino-5-(4'-methoxyphenyl)pyrazole;
1-benzyl-3,4-diamino-5-(3'-methoxyphenyl)pyrazole;
1-benzyl-3,4-diamino-5-(2'-methoxyphenyl)pyrazole;
1-benzyl-3,4-diamino-5-(4'-methylphenyl)pyrazole;
1-benzyl-3,4-diamino-5-(3'-methylphenyl)pyrazole;
1-benzyl-3,4-diamino-5-(2'-chlorophenyl)pyrazole;
1-benzyl-3,4-diamino-5-(4'-chlorophenyl)pyrazole;
1-benzyl-3,4-diamino-5-(3'-trifluoromethylphenyl) pyrazole;
1-[4'-chlorobenzyl]-3,4-diamino-5-methylpyrazole;
1-[4'-chlorobenzyl]-3,4-diamino-5-ethylpyrazole;
1-[4'-chlorobenzyl]-3,4-diamino-5-tert-butylpyrazole;
1-[4'-chlorobenzyl]-3,4-diamino-5-phenylpyrazole;
1-[4'-chlorobenzyl]-3,4-diamino-5-methoxypyrazole;
1-[4'-chlorobenzyl]-3,4-diamino-5-(4'-methoxyphenyl) pyrazole;
1-[4'-chlorobenzyl]-3,4-diamino-5-(3'-methoxyphenyl) pyrazole;
1-[4'-chlorobenzyl]-3,4-diamino-5-(2'-methoxyphenyl) pyrazole;
1-[4'-chlorobenzyl]-3,4-diamino-5-(4'-methylphenyl) pyrazole;
1-[4'-chlorobenzyl]-3,4-diamino-5-(3'-methylphenyl) pyrazole;
1-[4'-chlorobenzyl]-3,4-diamino-5-(2'-chlorophenyl) pyrazole;
1-[4'-chlorobenzyl]-3,4-diamino-5-(4'-chlorophenyl) pyrazole;
1-[4'-chlorobenzyl]-3,4-diamino-5-(3'-trifluoromethylphenyl)pyrazole;
3,4-diamino-5-hydroxymethyl-1-methylpyrazole;
3,4-diamino-5-hydroxymethyl-1-ethylpyrazole;
3,4-diamino-5-hydroxymethyl-1-isopropylpyrazole;
3,4-diamino-5-hydroxymethyl-1-propylpyrazole;
1-benzyl-3,4-diamino-5-hydroxymethylpyrazole;
1-[4'-chlorobenzyl]-3,4-diamino-5-hydroxymethylpyrazole;
5-aminomethyl-3,4-diamino-1-methylpyrazole;
5-aminomethyl-3,4-diamino-1-ethylpyrazole;
5-aminomethyl-3,4-diamino-1-isopropylpyrazole;
5-aminomethyl-3,4-diamino-1-propylpyrazole;
5-aminomethyl-1-benzyl-3,4-diaminopyrazole;
5-aminomethyl-1-[4'-chlorobenzyl]-3,4-diaminopyrazole;
3,4-diamino-5-hydroxymethylpyrazole;
3,4-diamino-5-[β-hydroxyethylamino]-1-methylpyrazole;
3,4-diamino-5-[β-hydroxyethylamino]-1-ethylpyrazole;
3,4-diamino-5-[β-hydroxyethylamino]-1-isopropylpyrazole;
3,4-diamino-5-[β-hydroxyethylamino]-1-propylpyrazole;
3,4-diamino-5-[β-hydroxyethylamino]pyrazole;
1-benzyl-3,4-diamino-5-[β-hydroxyethylamino]pyrazole;
1-[4'-chlorobenzyl]-3,4-diamino-5-[β-hydroxyethylamino]pyrazole;
3,4-diamino-5-isopropyl-1-methylpyrazole;
or an acid addition salt of any of said compounds.

6. A composition according to claim 5, wherein the 5-substituted 3,4-diaminopyrazole of formula I is:
3,4-diamino-5-methylpyrazole;
3,4-diamino-5-ethylpyrazole;
3,4-diamino-5-isopropylpyrazole;
3,4-diamino-5-tert-butylpyrazole;
3,4-diamino-5-phenylpyrazole;
3,4-diamino-5-(4'-methoxyphenyl)pyrazole;
3,4-diamino-5-(3'-methoxyphenyl)pyrazole;
3,4-diamino-5-(2'-methoxyphenyl)pyrazole;
3,4-diamino-5-(4'-methylphenyl)pyrazole;
3,4-diamino-5-(3'-methylphenyl)pyrazole;
5-(2'-chlorophenyl)-3,4-diaminopyrazole;
5-(4'-chlorophenyl)-3,4-diaminopyrazole;
3,4-diamino-1,5-dimethylpyrazole;
3,4-diamino-5-ethyl-1-methylpyrazole;
3,4-diamino-5-isopropyl-1-methylpyrazole;
3,4-diamino-1-methyl-5-tert-butylpyrazole;
3,4-diamino-1-methyl-5-phenylpyrazole;
3,4-diamino-1-methyl-5-methoxypyrazole;
3,4-diamino-1-methyl-5-(4'-methoxyphenyl)pyrazole;
3,4-diamino-1-methyl-5-(3'-methoxyphenyl)pyrazole;
3,4-diamino-1-methyl-5-(2'-methoxyphenyl)pyrazole;
3,4-diamino-1-methyl-5-(4'-methylphenyl)pyrazole;
3,4-diamino-1-methyl-5-(3'-methylphenyl)pyrazole;
5-(2'-chlorophenyl)-3,4-diamino-1-methylpyrazole;
5-(4'-chlorophenyl)-3,4-diamino-1-methylpyrazole;
or an acid addition salt of any of said compounds.

7. A composition according to claim 1, wherein said halogenated meta-aminophenol of formula II is 3-amino-6-chlorophenol, 3-amino-6-bromophenol, 3-(β-aminoethyl)

amino-6-chlorophenol, 3-(β-hydroxyethyl)amino-6-chlorophenol, 3-amino-2-chloro-6-methylphenol, or an acid addition salt of any of said compounds.

8. A composition according to claim 1, wherein said 5-substituted 3,4-diaminopyrazole of formula I and/or said acid addition salt represent from 0.0005 to 12% by weight of the total weight of the dyeing composition.

9. A composition according to claim 8, wherein said 5-substituted 3,4-diaminopyrazole of formula I and/or said acid addition salt represent from 0.005 to 6% by weight of the total weight of the dyeing composition.

10. A composition according to claim 1, wherein said halogenated meta-aminophenol of formula II and/or said acid addition salt represent from 0.0001 to 5% by weight of the total weight of the dyeing composition.

11. A composition according to claim 10, where the halogenated meta-aminophenol of formula II and/or said acid addition salt represent from 0.005 to 3% by weight of the total weight of the dyeing composition.

12. A composition according to claim 1, wherein said acid addition salts are hydrochlorides, hydrobromides, sulphates, tartrates, lactates or acetates.

13. A composition according to claim 1, wherein said appropriate medium for dyeing comprises water or a mixture of water and at least one organic solvent, wherein said organic solvent is a $C_1$–$C_4$ lower alkanol, a glycerol, a glycol, a glycol ether, an aromatic alcohol, or a mixture thereof.

14. A composition according to claim 1, wherein said composition has a pH ranging from 3 to 12.

15. A composition according to claim 1, wherein said composition is in the form of a liquid, a cream, a gel, or in another form appropriate for dyeing keratinous fibres.

16. A composition according to claim 15, wherein the keratinous fibres are human hair.

17. A method for dyeing keratinous fibres, said method comprising applying a composition according to claim 1 to said keratinous fibres for a time sufficient to develop a colr, said method further comprising developing said color at acidic, neutral, or alkaline pH in the presence of an oxidizing agent which is added to the dye composition only at the time of said developing or which is present in an oxidizing composition that is applied:

(i) separately from the dye composition at the same time that said dye composition is applied to said fibres, or (ii) sequentially with the dye composition.

18. A method according to claim 17, wherein the keratinous fibres are human hair.

19. A method according to claim 17, where said oxidizing agent is hydrogen peroxide, urea peroxide, an alkali metal bromate, a persalt, or a peracid.

20. A method according to claim 19, wherein said persalt is a perborate, a percarbonate or a persulphate.

21. A method according to claim 17, wherein said dyeing composition is applied to said keratinous fibres for a time ranging from 3 to 60 minutes.

22. A method according to claim 21, wherein said dyeing composition is applied to said keratinous fibres for a time ranging from 5 to 40 minutes.

23. A multicompartment device or multicompartment dyeing kit, comprising in a first compartment a dyeing composition according to claim 1 and in a second compartment an oxidizing composition.

* * * * *

UNITED STATES PATENT AND TRADEMARK OFFICE
CERTIFICATE OF CORRECTION

PATENT NO. : 6,090,162
DATED : July 18, 2000
INVENTORS : Mireille MAUBRU

It is certified that error appears in the above-identified patent and that said Letters Patent is hereby corrected as shown below:

On the Title Page, Item [54], in the Title, line 5, after "META-AMINOPHENOL," INSERT --, AND METHOD OF DYEING--.

In Claim 17, col. 16, line 5, "colr" should read --color--.

Signed and Sealed this

Seventeenth Day of April, 2001

Attest:

NICHOLAS P. GODICI

*Attesting Officer*    Acting Director of the United States Patent and Trademark Office